United States Patent [19]
Stalling

[11] Patent Number: 5,948,307
[45] Date of Patent: Sep. 7, 1999

[54] HIGH PRESSURE RELIEF FOR MICROWAVE DIGESTION VESSEL ASSEMBLY

[75] Inventor: David L. Stalling, Columbia, Mo.

[73] Assignee: O.I. Corporation, College Station, Tex.

[21] Appl. No.: 08/868,756

[22] Filed: Jun. 4, 1997

[51] Int. Cl.$^6$ .................................................... H05B 6/64
[52] U.S. Cl. .......................... 219/686; 219/687; 422/102
[58] Field of Search .................................. 422/102, 119, 422/242; 219/686, 687

[56] References Cited

U.S. PATENT DOCUMENTS

| | | | |
|---|---|---|---|
| 2,489,787 | 11/1949 | Knowlton | 220/89 |
| 2,924,354 | 2/1960 | Hansen | 220/89 |
| 3,080,091 | 3/1963 | Philip | 220/89 |
| 3,618,807 | 11/1971 | Rownd | 220/10 |
| 4,073,402 | 2/1978 | Wood | 220/207 |
| 4,151,253 | 4/1979 | Waggoner et al. | 422/68 |
| 4,192,192 | 3/1980 | Schnell | 73/715 |
| 4,248,831 | 2/1981 | Hughes | 422/102 |
| 4,590,957 | 5/1986 | McFarlane | 137/68.1 |
| 4,613,738 | 9/1986 | Saville | 219/10.55 |
| 4,655,070 | 4/1987 | Clift | 72/325 |
| 4,672,996 | 6/1987 | Floyd et al. | 137/522 |
| 4,736,083 | 4/1988 | Saville | 219/10.55 |
| 4,877,624 | 10/1989 | Floyd et al. | 426/241 |
| 4,882,128 | 11/1989 | Hukvari et al. | 422/119 |
| 4,904,450 | 2/1990 | Floyd | 422/113 |
| 4,919,819 | 4/1990 | Robinson et al. | 210/662 |
| 4,933,529 | 6/1990 | Saville | 219/10.55 |
| 4,944,923 | 7/1990 | Heinrichs et al. | 422/102 |
| 5,204,065 | 4/1993 | Floyd | 422/113 |
| 5,230,865 | 7/1993 | Hargett et al. | 422/102 |
| 5,264,185 | 11/1993 | Floyd | 422/113 |

*Primary Examiner*—Tu Ba Hoang
*Attorney, Agent, or Firm*—Arnold White & Durkee

[57] ABSTRACT

A high pressure and temperature microwave digestion vessel assembly with enhanced safety features is disclosed. The assembly includes a membrane that is rupturable for pressure relief, and a secondary pressure relief mechanism including a seal cap with an annular stress relief region that shears or fractures when excess pressure is in the vessel interior. The membrane is positioned on a post extending from the seal cap into the inner liner. The diameter of the venting orifice may be adjusted to vary the desired pressure relief. The assembly also includes a piercing mechanism for venting the vessel after digestion is completed.

8 Claims, 6 Drawing Sheets

HIGH PRESSURE RELIEF FOR MICROWAVE DIGESTION VESSEL ASSEMBLY

BACKGROUND OF THE INVENTION

1. Field of the Invention

This invention relates to pressure relief in a high pressure and high temperature microwave digestion assembly. The assembly is particularly adapted for use in a microwave oven and permits safe and effective chemical digestion of sample material for the purpose for chemical analysis.

2. Description of Related Art

Microwave heating and digestion of organic samples in enclosed high pressure and high temperature vessels has greatly shortened the amount of time required to perform chemical analysis. Ventable containers are especially useful for holding analytical samples which are being digested by treatments with strong chemicals, such as nitric, hydrochloric and sulfuric acids. In such heatings and digestions it is often important to keep the digestion vessel sealed to prevent contamination and to prevent losses of materials and reaction products. As heating and digestion proceed the internal pressure of the container normally increases, as material therein is vaporized. Typically, several vessels are used at one time, with a control vessel having temperature and/or pressure sensors therein for providing such information to the operator, which is intended to be representative of temperature and pressure in other sample vessels as well. However, despite the availability of temperature and pressure data, excessive pressure can develop in one or more vessels. To prevent damage to the vessel by development of excessive pressure, a rupture diaphragm or membrane can be used to vent gas and or liquid at a pressure lower than that which will cause significant damage to the container (and possibly to operators using it).

Microwave digestions of various materials, utilizing strong digesting agents, such as acids, are known and open vessel digestions of this type are described in 47 *Analytical Chemistry* 1475 (A. Abu Samra et al., 1975) and 50 Analytical Chemistry 1021 (P. Barrett et al., 1978). Closed system microwave digestions have also been practiced, as reported in 56 Analytical Chemistry 2233 (Nadkarni, 1984) and in Bureau of Mines Technical Progress Report No. 120 (S. A. Matthews et al., 1983). Savillex Corporation has marketed a lidded vessel for microwave digestions which is made of Teflon® PFA, obtainable from E.I. DuPont de nemours, Inc. and CEM Corporation has marketed pressure controlling accessories for use in microwave digestions in conjunction with its MDS-81 and MDS-81-D microwave systems.

U.S. Pat. No. 4,672,996 describes a relief valve for use on a container for material being digested in a microwave apparatus. A self-regulating valve positioned under a cap is threaded onto the vessel. The valve includes a pressure deformable, resilient wall member having a fluid vent port and an obstructing member which cooperates with the wall member to open the valve.

Other relief valves are disclosed in U.S. Pat. Nos. 4,400,401; 4,474,211; and 4,493,444.

Another pressure vessel is disclosed in U.S. Pat. No. 4,904,450. A replaceable, rupturable pressure release membrane is provided having predetermined rupture pressure. The membrane covers a vent to seal the container, and will rupture and release pressure within the container if that pressure reaches the predetermined rupture pressure.

Another microwave digestion vessel is disclosed in U.S. Pat. No. 4,613,738. This vessel includes a valve assembly including a ball valve with a vent opening in the lid of the vessel. When internal pressure becomes high enough to overcome the spring coefficient, the ball is unseated off the ball seat, and pressure flows around the circumference of the ball and through a vent.

U.S. Pat. No. 4,882,128 discloses a microwave digestion vessel which includes a sliding seal which is displaced from a sealing position into a non-sealing position when internal pressure exceeds a predetermined value.

U.S. Pat. No. 4,993,529 relates to a microwave digestion vessel including a valve assembly formed by a U-shaped exhaust hole in the cap. Pressure inside the digestion vessel forces a plunger up against the diaphragm, subsequently releasing pressure through an exhaust hole in the cap.

U.S. Pat. No. 5,230,865 discloses a ventable container for digestion including a rupture diaphragm in the venting passageway and enclosure for the ventable container. The diaphragm is tightenable into place so that the container is sealed and may be moved when desired to open and vent the container.

While the relief valves and membranes disclosed in the prior art permit improved control and safer microwave digestion, these devices can limit or restrict the available pressure relief. Digestion of samples containing considerable organic material or minerals that yield gaseous products undergo exothermic reactions that result in large pressure and temperature excursions in closed vessels. Strong mineral acids used in mixtures or in combination with additional oxidizing agents such as hydrogen peroxide increase the possibility that resulting pressures and volumes can exceed pressure relief available.

Depending on the pressure developed in the vessel during digestion, the relief valve or membrane may open or vent, but the vapors and entrained liquid flow through the vent or relief port may exceed the discharge capacity. Thus, the valves and venting mechanisms in the prior art have a definite risk that vapor or liquid will not be adequately vented until the vessel ruptures or fragments explosively.

Another limitation of existing microwave digestion vessels having rupturable membranes is that the membranes typically have been somewhat isolated from the sample in the reaction chamber. If the membrane was not at the same temperature and pressure as the sample, there was less predictability and more uncertainty as to rupture pressure.

Another limitation of microwave digestion vessels resulted from residual pressure after the digestion has been completed. Even if the membrane does not rupture, there still may be residual pressure of several hundred p.s.i in the vessel after digestion. This residual pressure can make it difficult to open the vessel and even dangerous when manually opening the vessel. For example, a wrench or other mechanical device may be required to unscrew the cap, even after the vessel is cooled down before it is opened.

SUMMARY OF THE INVENTION

It is a principal object of this invention to provide a safer microwave digestion vessel assembly with enhanced performance and reliability for use in high pressure microwave sample digestions. Another object of the invention is to provide a microwave digestion vessel which permits precise control of temperature and pressure. Another object of the invention is to provide a microwave digestion vessel which will allow adjustment of the pressure release point to various temperature and pressure parameters encountered in routine sample preparation. Another object of the invention is to provide a microwave digestion assembly which provides secondary pressure relief when internal pressure exceeds the capacity of the primary pressure relief mechanism.

These and other objects of the present invention are achieved by providing a high temperature, high pressure microwave digestion vessel comprising a container within which digestion is to take place under high temperature and high pressure conditions. The container is provided with a rupturable membrane as the primary pressure relief mechanism and a seal cap with an annular stress relief region as the secondary pressure relief mechanism. When the seal cap is sheared or fractured around the stress relief region due to excessive internal pressure, vapor and liquid may escape the vessel without damage to the structural integrity of the vessel or risk of danger to the operator.

The invention also includes a device for puncturing the membrane to release residual pressure in the vessel after digestion is completed.

The invention provides primary and secondary pressure relief mechanisms that may be used for a microwave digestion vessel with or without temperature and/or pressure sensors in the vessel. The secondary pressure relief mechanism will prevent damage to the vessel by releasing internal pressure before such damage occurs.

DETAILED DESCRIPTION OF A PREFERRED EMBODIMENT

Figure 1:
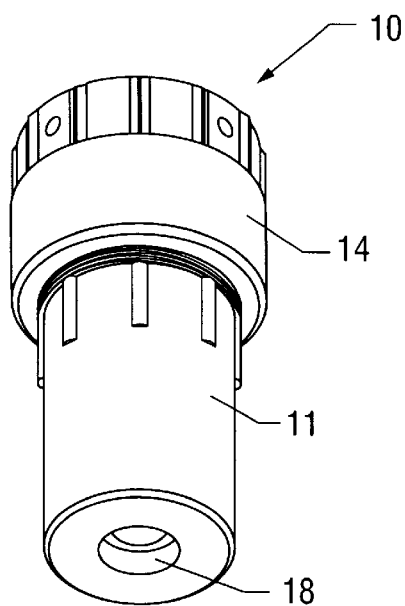
FIG. 1 is an isometric view of the microwave digestion vessel assembly.

Referring to FIG. 1 of the drawings, a microwave digestion vessel assembly (10) is illustrated. The microwave digestion vessel assembly includes a cylindrical outer casement (11) molded of microwave transparent material and preferably polyetherimide resin. Outer casement (11) has an access opening (18) in the bottom wall thereof which can be used to urge out cylindrical inner liner (12) positioned therein. Inner liner (12) preferably is molded of PFA Teflon, a chemically inert material which also is resistant to degradation under high temperature and pressure. The inner liner is sized to fit in close surface contact into outer casement (11). Outer cap (14), preferably molded of microwave transparent material such as polyetherimide resin, is attached with threads or other attachment means to outer casement (11).

Figure 2:
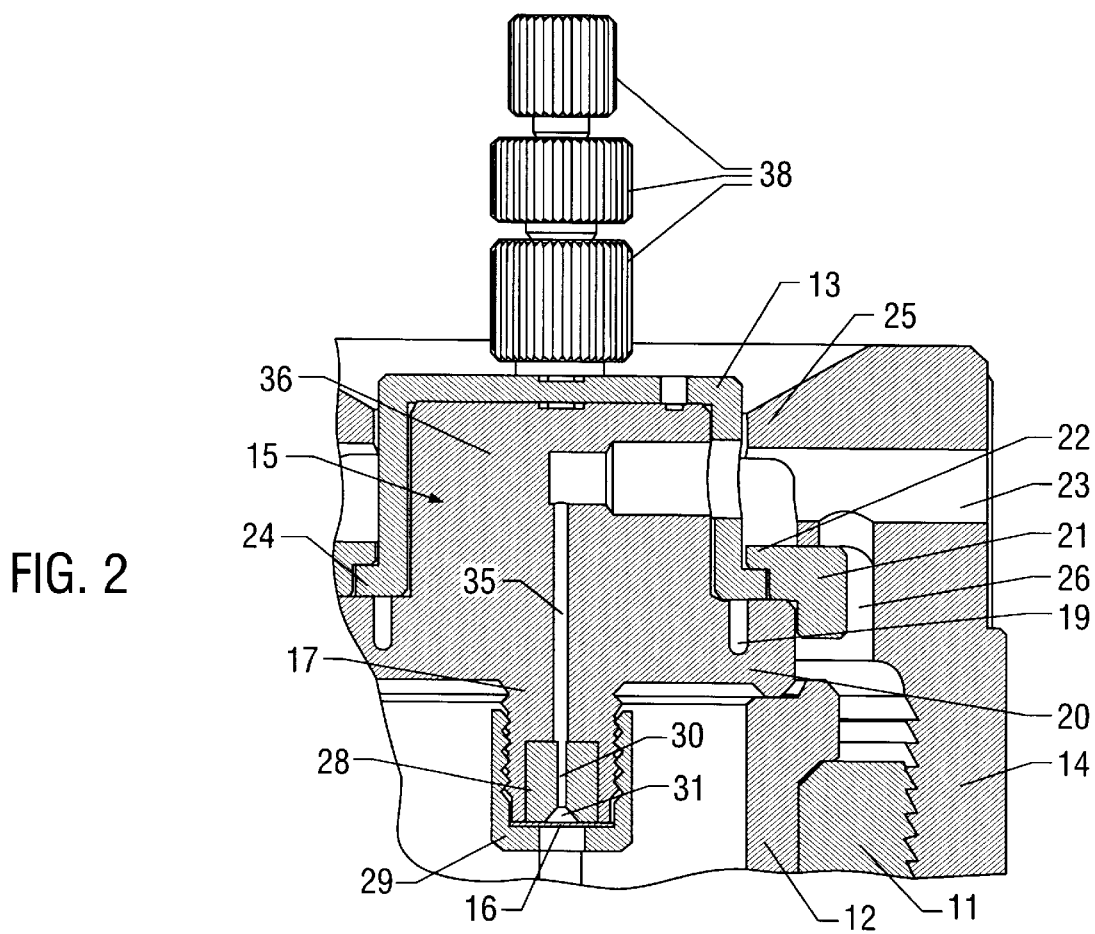
FIG. 2 is a cross section view of the seal cap, outer cap and hub of a control vessel for microwave digestion of samples with two-stage pressure relief according to a first embodiment of the invention.
Figure 3:
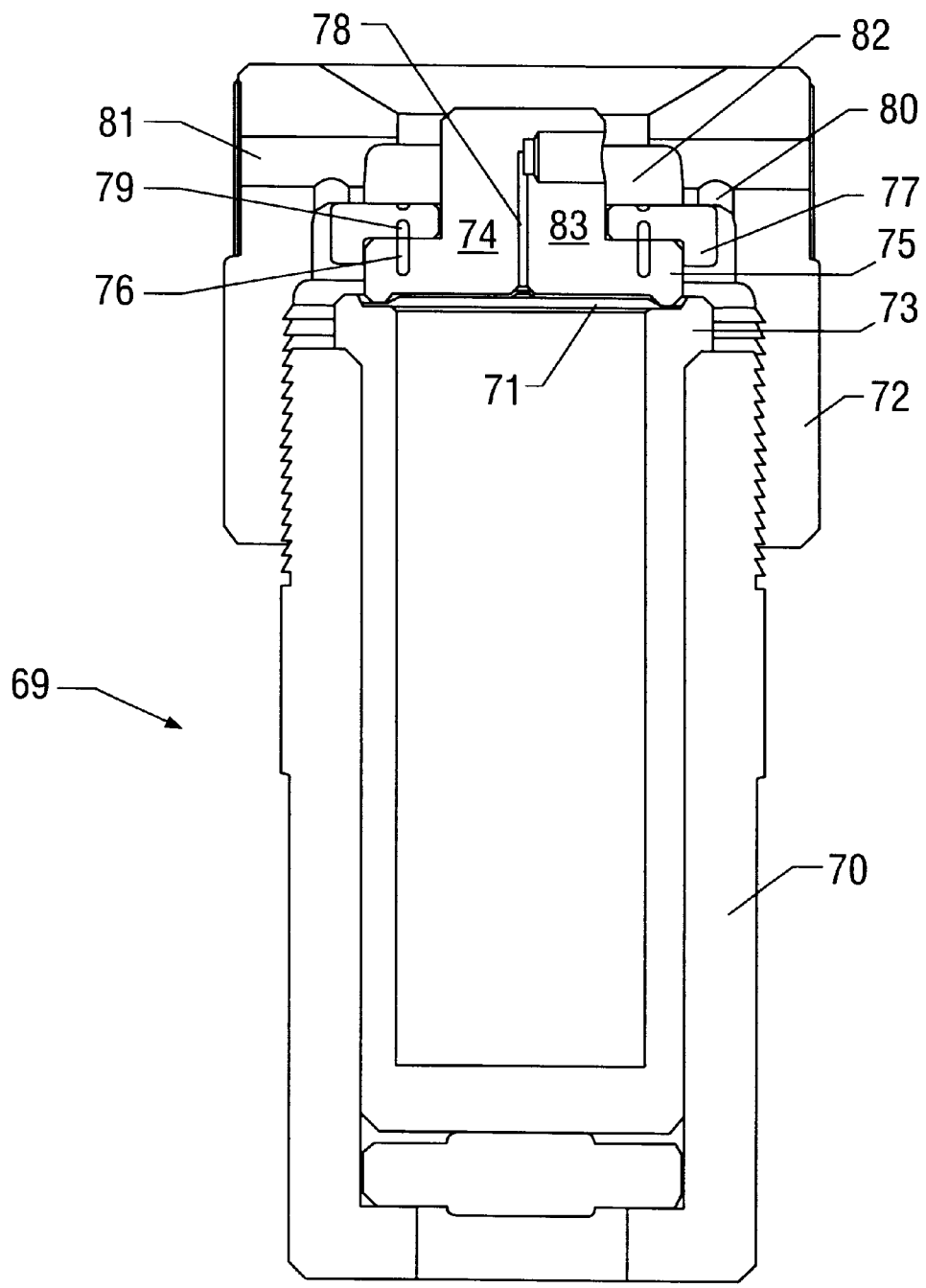
FIG. 3 is a cross section view of the microwave digestion sample vessel according to a second embodiment of the invention.

The two-stage pressure relief apparatus of the present invention may be used in a control vessel or sample vessel for microwave digestion. A control vessel typically includes a pressure sensor, temperature sensor and/or other components for providing information concerning the characteristics and parameters of the sample contained in the vessel. This information is intended to be representative of the parameters of other vessels holding the same or similar samples subject to digestion. Typically, each of the sensors may be inserted through a passage in the seal cap which covers the open end of the inner liner, and into the interior of the vessel. The embodiment of FIG. 2 illustrates a first embodiment of the invention where the two-stage pressure relief apparatus is used in a control vessel. The second embodiment shown in FIG. 3 illustrates the two-stage pressure relief apparatus of the present invention in a sample vessel (i.e., without temperature and/or pressure sensors.)

As shown in FIG. 2, seal cap (15) is positioned over the open end of inner liner (12) and is secured by tightening outer cap (14) to outer casement (11), to seal the seal cap to the inner liner. Fittings (38) for temperature and/or pressure sensors are threaded to the seal cap. Primary pressure relief is provided by rupturable membrane (16) which preferably is rupturable at approximately 700 p.s.i. at a temperature of 190 degrees C. The preferred apparatus for positioning and sealing the rupturable membrane in the control vessel is discussed in detail below.

Still referring to FIG. 2, the seal cap includes flange (20) and center portion (36). Annular stress relief region (19) is preferably a groove in the flange (20) of the seal cap. This annular stress relief region provides secondary pressure relief under conditions when pressure relief available through the rupturable membrane (16) and vent passage (35) is insufficient, such as when the membrane fails to rupture, venting passages are obstructed, or at higher pressures and/or sample volumes. Although a groove is the preferred configuration of the stress relief region, other geometric may be used to provide a stress relief region in the seal cap, that will shear or fracture before other components of the vessel break or become damaged. If pressure at a given temperature exceeds other pressure relief available, and before the other components of the vessel break or are damaged, pressure in the vessel urges center portion (36) of the seal cap away from the open end of the inner liner, until flange (20) of seal cap (15) shears or fractures around the annular stress relief region or groove (19). When center portion (36) of the seal cap is forced away from the open end of the inner liner, and flange (20) shears or fractures, a pressure relief path is created through pressure relief ports (26) and auxiliary vent ports (23). Preferably the annular stress relief region or groove (19) has a thickness less than one half of the thickness of flange (20). In the preferred embodiment of FIG. 2, the seal cap is made from PFA teflon and flange (20) has a thickness of 0.340 inches while annular stress relief region or groove (19) has a thickness of 0.100 inches.

In the microwave digestion vessel assembly shown in FIG. 2, excessive internal pressure also will shear to fracture flange (22) of safety washer (21). The safety washer fits around the outer surface of the seal cap and preferably is interposed between flange (20) and outer cap (14). Preferably, flange (22) has a thickness substantially less than that of the safety washer. In the embodiment of FIG. 2, safety washer (21) is made from polyetherimide resin (or other microwave transparent material) and has a thickness of 0.180 inches while flange (22) has a thickness of between 0.080 inches and 0.130 inches depending on maximum temperature of use. In the embodiment of FIG. 2, sufficiently high internal pressure in the vessel causes flange (21) to fracture around stress relief region (19) and safety washer

(21) to fracture around flange (22). The center portion (36) of the seal cap is then forced away from the open end of the inner liner until it is restrained when safety retaining lip (24) on hub (13) contacts shoulder (25) of outer cap (14). Shearing or fracturing of the secondary pressure relief mechanism described above allows gases or liquids to escape through auxiliary vent ports (26) and high pressure relief ports (23) connected to a vent tube or tubes (not shown) which direct the gas or liquid to an acid collector or reservoir.

In the microwave digestion vessel assembly of FIG. 2, an improved apparatus for retaining and securing rupturable membrane (16) also is shown. Membrane retainer (29) is removably attached to post extension (17) extending into the open end of the inner liner from the seal cap. Membrane retainer (29) is tightened by threads or other means to hold the membrane against the post extension (17). The post extension has a vent passage (35) extending therethrough which, upon rupture of the membrane, provides a path for gas or fluid to escape from the vessel through the seal cap. By positioning the rupturable membrane on the end of the post extension and retaining it there with the membrane retainer, the membrane is more visible and easily accessible for replacement, is located inside the inner liner near the sample being digested, is subject to the same temperature and pressure as the sample, and enhances predictability of rupture pressures and temperatures.

Still referring to FIG. 2, a selection of replaceable venting plugs (28) each having a different diameter orifice (30) may be inserted in post extension (17) of the seal cap to allow variation in desired rupture pressures and temperatures for the rupturable membrane. A venting plug having a larger orifice diameter will result in lower pressure required to rupture the membrane. Preferably, the venting plug is ¼ inch in length and the orifice diameter may vary from approximately 0.045 to 0.150 inches. The opposing ends of the orifice in each of the venting plugs also may have different diameters. By orienting the larger diameter end of the orifice to face the membrane, the membrane will rupture at a lower pressure. Additionally, the diameter of the cone or taper (31) at the end of the orifice helps determine rupture pressure, principally by eliminating shear at sharp corners that tend to cause premature membrane rupture.

FIG. 3 shows the two-stage pressure relief apparatus in a sample vessel according to a second embodiment of the invention. In this embodiment, the sample vessel (69) for microwave digestion lacks temperature or pressure probes. The sample vessel includes outer casement (70) which holds inner liner (73). Primary pressure relief is through rupturable membrane (71) which is positioned over the open end of the inner liner. Outer cap (72) is tightened to the outer casement to secure the rupturable membrane at its outer circumference to the open end of the inner liner and form a sealing relationship between seal cap (74), membrane (71), and inner liner (73). When pressure in the vessel exceeds a predetermined pressure, the membrane ruptures and gas or fluid may escape through vent passage (78) in the seal cap and pressure relief ports (81). For secondary pressure relief, seal cap flange (75) includes an annular stress relief groove (76) that will provide stress relief in response to pressure inside the vessel before other vessel components break or result in damage the vessel (i.e., when the membrane fails to rupture, the venting passage is obstructed, or when pressure or volume exceeds the pressure relief available through vent passage (78)). Excess pressure in the vessel urges the center portion (83) of the seal cap away from the inner liner until flange (75) stretches and fractures around stress relief groove (76). Preferably, safety washer (77) around the outer circumference of the seal cap includes annular stress relief groove (79) which also fractures when pressure exceeds that which is relieved through the rupturable membrane and/or passage (78) but below that which results in damage to other components of the sample vessel. The secondary pressure relief mechanism allows fluid and/or gas to escape from the vessel through passages (80) and pressure relief ports (81).

In tests of microwave digestion vessel assemblies having the secondary high pressure relief mechanism of the present invention, fracture of the stress relief region occurred at internal pressures of 1000 to 1200 p.s.i., at 185 degrees C. However, the internal pressure in the vessel sufficient to fracture the stress relief region will depend on the particular components used and digestion application involved. The invention is not limited to any particular range of pressures or temperatures, but only to a secondary high pressure relief mechanism in the seal cap that will be sufficiently weaker than other vessel components so that fracture will predictably occur before damage to other vessel components.

Figure 4:
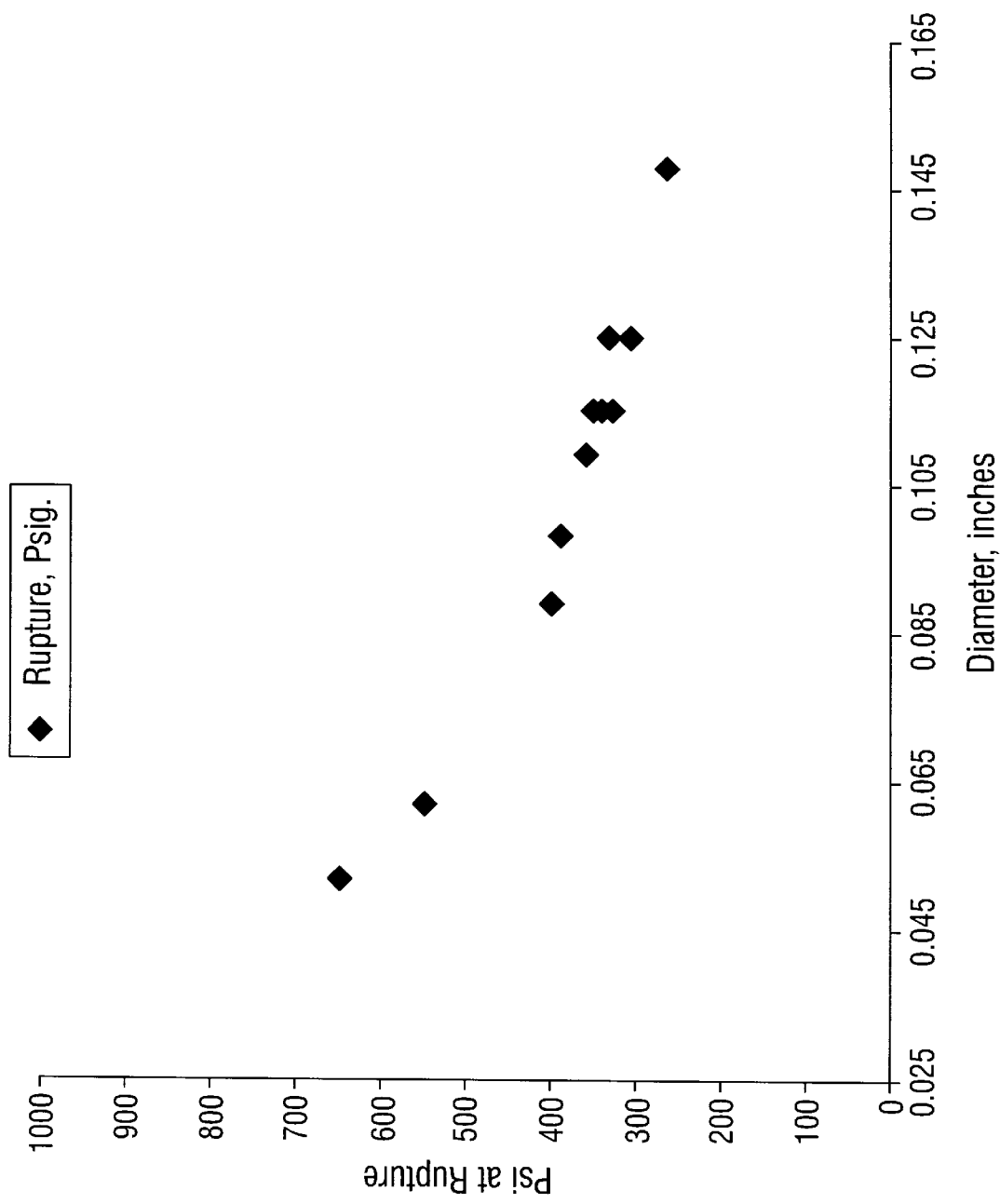
FIG. 4 is a graph illustrating the relationship between the rupture pressure of the membrane and orifice diameter of the vent plug according to the first embodiment.

The relationship between the rupture pressure of the primary pressure relief mechanism and the diameter of the orifice in venting plugs (28) is illustrated in the graph shown in FIG. 4. When used with a 0.010 inch thick PFA teflon membrane and an orifice diameter of 0.062 inches, rupture of the membrane occurred at pressures of between 500–600 p.s.i., while rupture occurred at between 600–700 p.s.i. when the orifice diameter was 0.052 inches (at internal temperatures of 185–195 degrees C). For higher pressure applications, the venting plug preferably has a face diameter of 0.125 inches with an orifice diameter of 0.052 inches, and the rupture pressure was 750 p.s.i. at 190 degrees C. For lower pressure microwave digestion applications, the venting plug preferably has a face diameter of 0.250 inches and an orifice diameter of 0.125 inches, and the rupture pressure was between 315–330 p.s.i. at 125–150 degrees C.

Figure 5A:
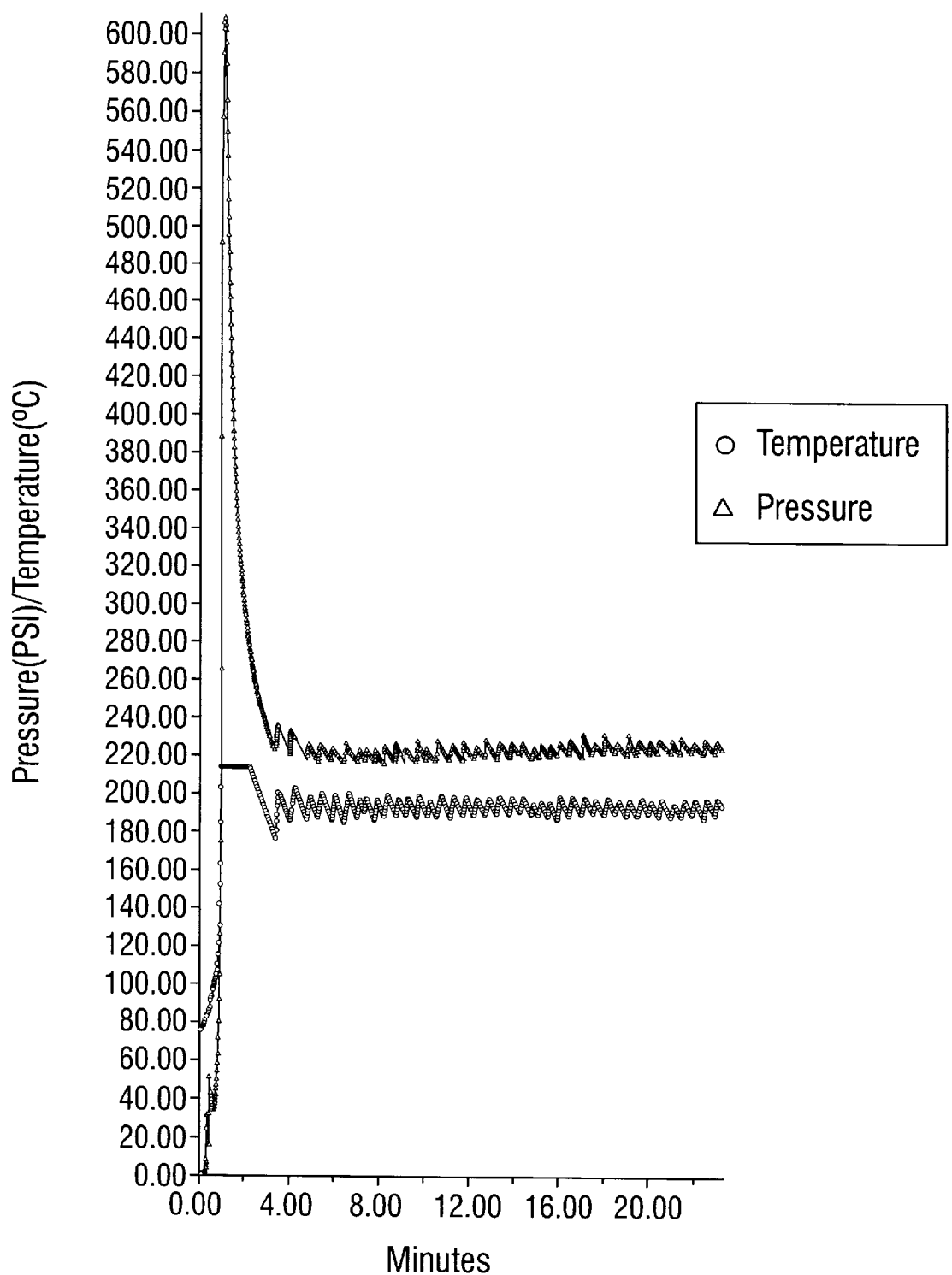
FIGS. 5 (a) and (b) show the temperature and pressure profiles for the digestion of desiccated liver using 5.0 mL nitric acid and 2.0 mL of hydrogen peroxide, using the primary pressure relief apparatus of the invention.
Figure 5B:
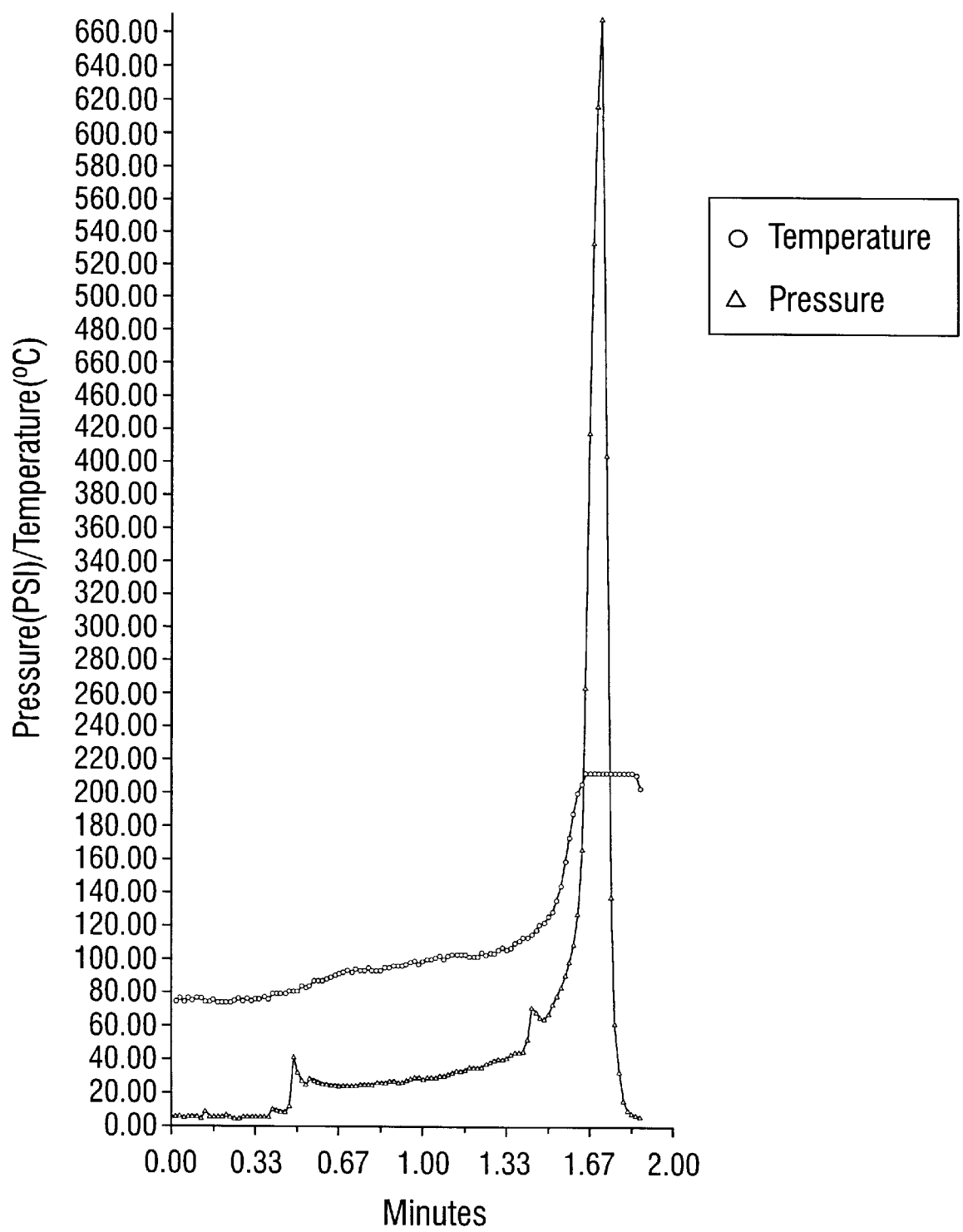

FIGS. 5 (a) and 5(b) show recorded pressure and temperature profiles for the primary pressure relief mechanism during microwave digestion of desiccated liver using 5.0 mL nitric acid and 5.0 mL of hydrogen peroxide in the vessel. As shown in FIG. 5 (a), for the 0.052 inch diameter rupture orifice, microwave digestion of a sample size of 0.60 grams did not rupture the membrane or fracture the secondary pressure relief mechanism. As shown in FIG. 5(b), digestion of another sample of 0.755 grams of dried liver resulted in rupture of the membrane at a pressure of 660–670 p.s.i.

Figure 6:
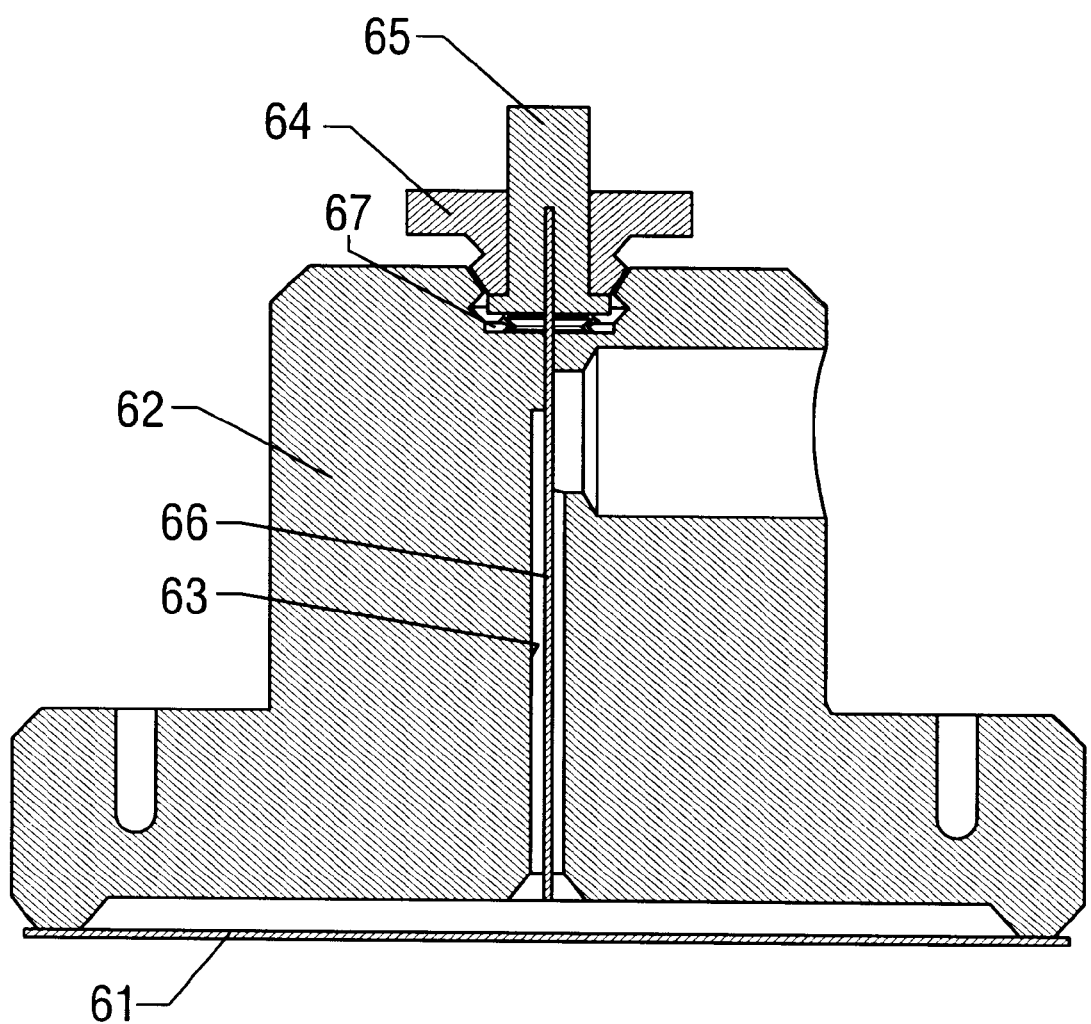
FIG. 6 is a cross section view of the piercing fiber and plunger assembly according to a preferred embodiment of the invention.

Now referring to FIG. 6, piercing fiber (66) can be used to relieve pressure after digestion by compressing plunger (65) in seal cap (62) which forces the piercing fiber through membrane (61). The seal cap has a vent passage (63) with a retaining nut (64) threaded to the top of the seal cap. Plunger (65) is inserted through the nut. The piercing fiber (66) is preferably quartz or may be a heated fiber. Bellows spring (67) is preferably PFA or plastic and holds the plunger in the retracted position until it is used.

A high temperature and high pressure microwave digestion vessel assembly is described. Various details of the invention may be changed without departing from its scope. Furthermore, the foregoing description of the preferred embodiments of the invention and the best mode for practicing the invention is provided for the purpose of illustration only and not for purpose of limitation.

What is claimed is:

1. A microwave digestion vessel comprising:
   (a) an outer casement;
   (b) an inner liner positioned inside the outer casement; the inner liner having an open end;

(c) an outer cap removably attached to the outer casement;

(d) a seal cap positioned to seal the open end of the inner liner and secured against the open end of the inner liner by tightening the outer cap to the outer casement, the seal cap having a vent passage therethrough; and (e) a stress relief region in the seal cap located radially inside the open end of the inner liner where the seal cap is secured, the stress relief region having a thickness less than the thickness of the seal cap; the seal cap fracturable around the stress relief region in response to internal pressure to vent the inner liner before fracture of the outer casement, inner liner, or outer cap.

2. The microwave digestion vessel of claim 1 wherein the stress relief region is an annular groove around the seal cap.

3. The microwave digestion vessel of claim 1 further comprising:

(a) a post extending from the seal cap into the open end of the inner liner, the vent passage extending through the post;

(b) a membrane positionable on the end of the post to cover the vent passage; the membrane rupturable to vent the inner liner through the vent passage in response to internal pressure lower than the pressure at which the stress relief region is fractured; and (c) a membrane retainer removably attached to the post for retaining the membrane against the post, the membrane retainer having a passage therethrough.

4. The microwave digestion vessel of claim 3 further comprising a replaceable venting plug positionable in the post, the venting plug having an orifice which is concentric with the vent passage when the venting plug is positioned in the post.

5. The microwave digestion vessel of claim 1 wherein the outer cap has a high pressure relief port alignable with the vent passage in the seal cap.

6. The microwave digestion vessel of claim 1 further comprising a safety washer around the seal cap, the safety washer having a flange less than the thickness of the safety washer.

7. The microwave digestion vessel of claim 1 further comprising membrane piercing means insertable through the vent passage.

8. The microwave digestion vessel of claim 1 wherein the outer cap has a flange for limiting travel of the seal cap away from the inner liner when the seal cap fractures around the stress relief region.

* * * * *